United States Patent [19]

Patchett et al.

[11] Patent Number: 4,512,979

[45] Date of Patent: Apr. 23, 1985

[54] DIPEPTIDES CONTAINING THIALYSINE AND RELATED AMINO ACIDS AS ANTIHYPERTENSIVES

[75] Inventors: Arthur A. Patchett, Westfield; Mu T. Wu, Clark, both of N.J.

[73] Assignee: Merck & Co., Inc., Rahway, N.J.

[21] Appl. No.: 341,741

[22] Filed: Jan. 26, 1982

Related U.S. Application Data

[63] Continuation-in-part of Ser. No. 246,532, Mar. 23, 1981, abandoned.

[51] Int. Cl.$^3$ ............... A61K 37/00; C07C 103/52
[52] U.S. Cl. ........................ 514/2; 260/112.5 R
[58] Field of Search ............... 424/177; 260/112.5 R

[56] References Cited

U.S. PATENT DOCUMENTS 4,052,511 10/1977 Cushman et al. ............... 424/177

FOREIGN PATENT DOCUMENTS

| | | |
|---|---|---|
| 0012401 | 6/1980 | European Pat. Off. ..... 260/112.5 R |
| 2704985 | 2/1976 | Fed. Rep. of Germany ...... 424/177 |
| 2720996 | 5/1976 | Fed. Rep. of Germany ...... 424/177 |
| 2810261 | 3/1977 | Fed. Rep. of Germany ...... 424/177 |

Primary Examiner—Delbert R. Phillips
Attorney, Agent, or Firm—Salvatore C. Mitri; Michael C. Sudol; Mario A. Monaco

[57] ABSTRACT

The invention relates to dipeptide compounds containing thialysine and related amino acids which are useful as converting enzyme inhibitors and as antihypertensives.

14 Claims, No Drawings

DIPEPTIDES CONTAINING THIALYSINE AND RELATED AMINO ACIDS AS ANTIHYPERTENSIVES

BACKGROUND OF INVENTION

This is a continuation-in-part application of application Ser. No. 246,532 filed Mar. 23, 1981, now abandoned.

The invention in its broad aspects relates to dipeptide compounds containing thialysine and related amino acids which are useful as converting enzyme inhibitors and as antihypertensives. The compounds of this invention are represented by the following formula:

$$\underset{RO-\overset{O}{\overset{\|}{C}}-\overset{R_1}{\overset{|}{CH}}-NH-\overset{(CH_2)_l}{\overset{|}{CH}}-\overset{X}{\overset{|}{CH}}-CON-\overset{A}{\overset{|}{CH}}-CO_2R_2}{} \quad (I)$$

wherein:

R and $R_2$ are independently hydrogen, loweralkyl, aralkyl;

$R_1$ is alkyl containing one to ten carbon atoms which include straight chain, branched, unsaturated and cyclic alkyl groups; substituted lower alkyl wherein the alkyl group has 1–6 carbon atoms and the substituent is amino, acylamino, loweralkylthio, arylthio, aryloxy, arylamino, or hydroxy; aralkyl, aralkenyl, heteroaralkyl or heteroaralkenyl wherein the alkyl portion has 1 to 5 carbon atoms such as, for example, phenethyl, cinnamyl, or indolylethyl; substituted aralkyl, aralkenyl, heteroaralkyl, or heteroaralkenyl wherein the alkyl or alkenyl group has 1 to 5 carbons optionally substituted by amino, acylamino or hydroxy and wherein the aryl or heteroaryl groups are optionally substituted by halo, dihalo, amino, aminoalkyl, hydroxy, lower alkoxy, aryloxy or lower alkyl;

X is S, S→O or O;

l is 1–2;

m is 2–3;

$$\overset{A}{\overset{|}{N}}-\overset{B}{\overset{|}{CH}}-CO_2R_2$$

is a grouping wherein:

A is cycloalkyl containing 4–8 carbons in the ring, aryl, aralkyl, heteroaryl, or heteroaralkyl;

B is hydrogen or loweralkyl; or

A and B can be joined together to form ring structures, including the part-structure N—CH—CO$_2$R$_2$, having the formulae:

<chemical structures> wherein:

$Q_1$ and $Q_2$, taken together, are $CH_2CH_2$, $CH_2CH_2CH_2$, $COCH_2$, $CH_2S$, $CH_2$—CH—$OR_3$, or $CH_2$—CH—$SR_3$ wherein $R_3$ is hydrogen, loweralkyl, aryl, aralkyl, or $$\overset{O}{\overset{\|}{C}}-NR_4R_5$$

wherein $R_4$ and $R_5$ are independently hydrogen, loweralkyl, or aralkyl;

W is a bond, CO, CH$_2$;

Z is a bond except when W is a bond, CO, CH$_2$, CH$_2$CH$_2$;

and, the pharmaceutically acceptable salts thereof.

The loweralkyl groups, except where noted otherwise, represented by any of the variables include straight and branched chain hydrocarbon radicals from one to six carbon atoms such as, for example, ethyl, isopentyl, allyl, cyclohexyl, and the like. Halo means chloro, bromo, iodo or fluoro. Acyl denotes lower alkanoyl or aroyl. Aryl, where it appears in any of the radicals, except where noted, represents phenyl, naphthyl, biphenyl, and the like, and heteroaryl groups include, for example, indolyl, imidazolyl, thienyl, furyl, pyridyl, and the like. Aralkyl groups are lower alkyl groups substituted by aryls such as phenyl and aroyl refers to such groups as benzoyl, p-chlorobenzoyl, and the like.

Preferred are those compounds of Formula I wherein:

R and $R_2$ are independently hydrogen, lower alkyl, aralkyl;

$R_1$ is alkyl containing one to eight carbon atoms both straight chain and branched; substituted loweralkyl wherein the alkyl group has 1–3 carbons and the substituent is arylthio, aryloxy; aralkyl, aralkenyl, heteroaralkyl, or heteroaralkenyl wherein the alkyl group has 1 to 5 carbon atoms and the aryl or heteroaryl group can be substituted by halo, dihalo, amino, aminoalkyl, hydroxy, loweralkoxy, aryloxy, or loweralkyl;

X is S or O;

l is 1 or 2;

m is 2 or 3; and,

A and B are joined together to form ring structures having the formulae:

<chemical structures> wherein:

$Q_1$ and $Q_2$, taken together, are $CH_2CH_2$, $CH_2S$, $COCH_2$, or $CH_2CHOR_3$ wherein $R_3$ is hydrogen or loweralkyl;

W is $CH_2$, CO; and,

Z is a bond or $CH_2$.

More preferred are those compounds of Formula I wherein

R and $R_2$ are hydrogen;

$R_1$ is aralkyl and heteroaralkyl wherein the alkyl group has 1 to 4 carbon atoms and the aryl or heteroaryl group can be sustituted by halo, dihalo, amino, aminoalkyl, hydroxy, lower alkoxy or lower alkyl;

X is S or O;

l is 1 or 2;

m is 2 or 3;

A and B are joined together to form ring structures having the formulae:

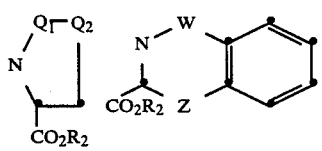

wherein:
$Q_1$ and $Q_2$, taken together, are $CH_2CH_2$, $CH_2S$, $COCH_2$, or $CH_2CHOR_3$ wherein $R_3$ is loweralkyl;
W is $CH_2$; and
Z is $CH_2$.

Most preferred are those compounds of Formula I wherein:
R and $R_2$ are hydrogen;
$R_1$ is aralkyl or heteroaralkyl wherein the alkyl group has 1–4 carbon atoms and the aryl or heteroaryl groups can be substituted by halo or hydroxy;
X is S or O;
l is 2;
m is 2;
A and B are joined together to form ring structures having the formulae:

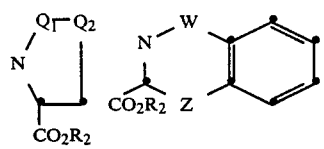

wherein:
$Q_1$ and $Q_2$, taken together, are $CH_2CH_2$ and $CH_2S$;
W is $CH_2$; and,
Z is $CH_2$.

The preferred, more preferred and most preferred compounds also include the pharmaceutically acceptable salts thereof.

The products of Formula I can be produced by the methods depicted in the following Reaction Schemes wherein R, $R_1$, $R_2$, $R_3$, $R_4$, $R_5$, A, B, $Q_1$, $Q_2$, X, W, Z, l, and m are as defined above unless otherwise indicated.

As will be evident to those skilled in the art and as demonstrated in the Examples, reactive groups not involved in the condensation reactions such as amino, hydroxyl, carboxy, etc. can be protected by methods standard in peptide chemistry and subsequently deblocked to afford the desired intermediates and final products.

REACTION SCHEME I

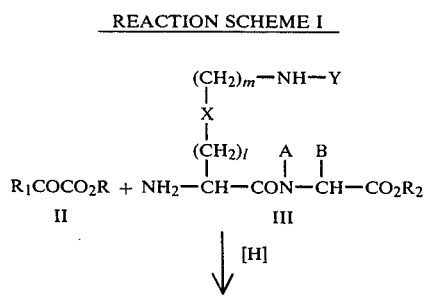

REACTION SCHEME I
-continued

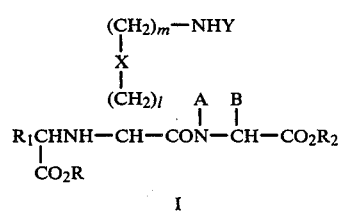

REACTION SCHEME II

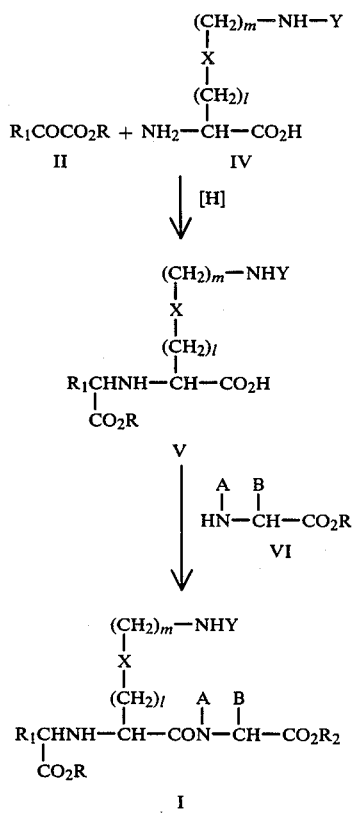

REACTION SCHEME III

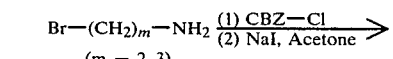

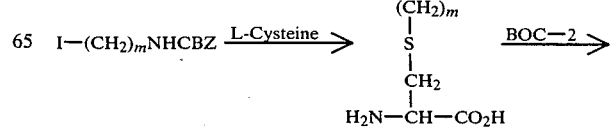

4,512,979
REACTION SCHEME III
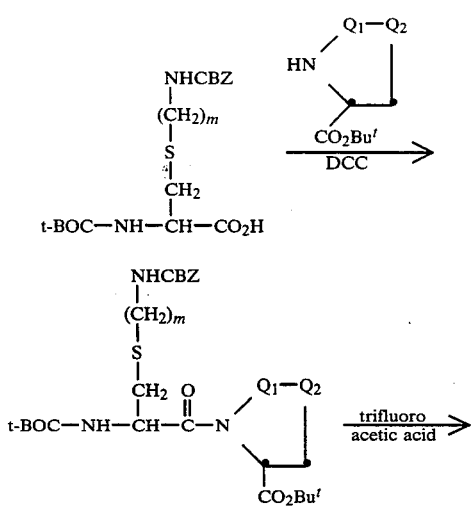
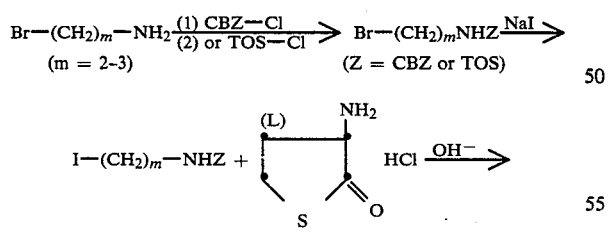
REACTION SCHEME IV, Method A
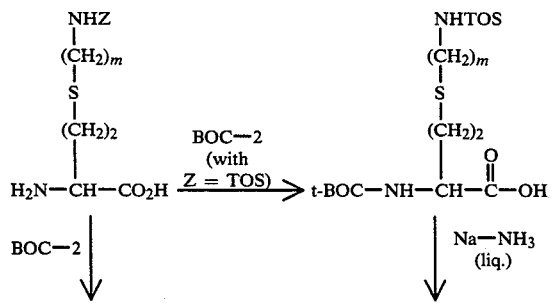
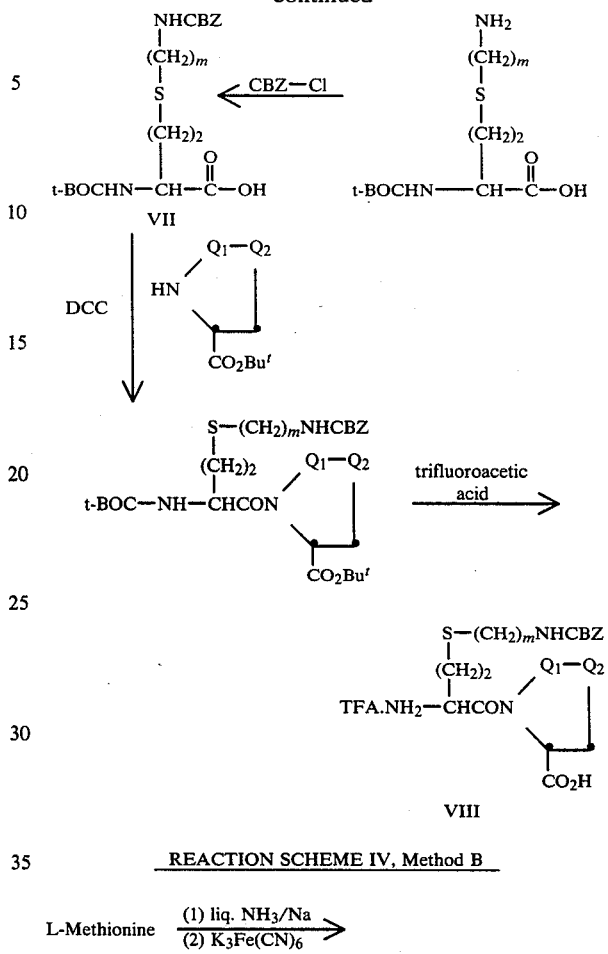
REACTION SCHEME IV, Method B
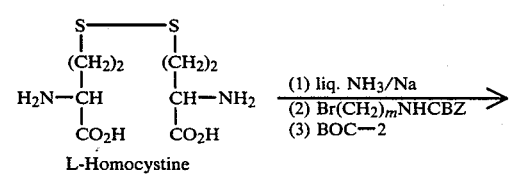
REACTION SCHEME V
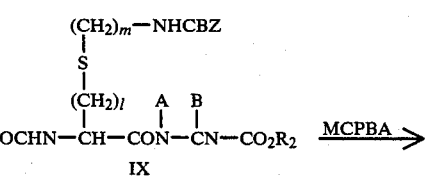

REACTION SCHEME V

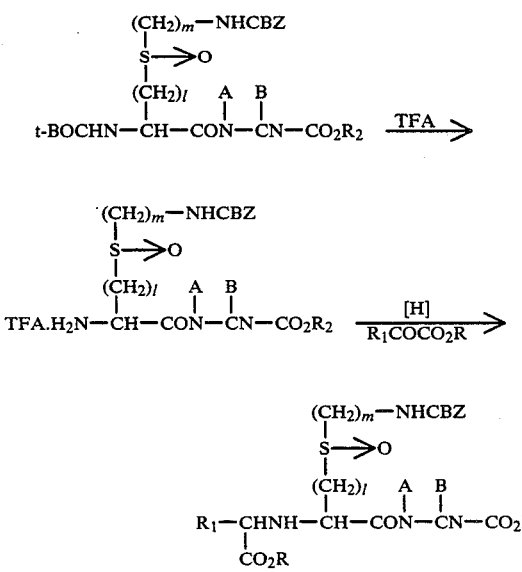

REACTION SCHEME VI

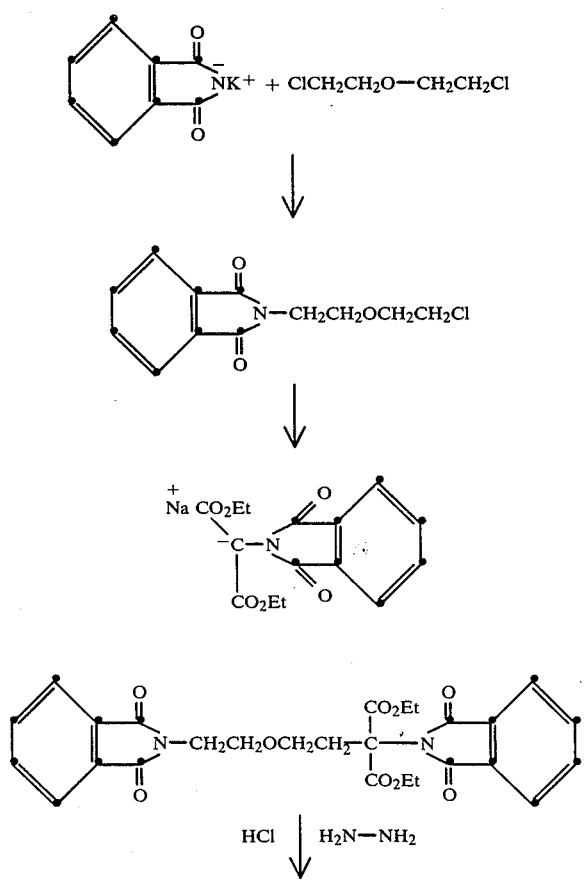

-continued
REACTION SCHEME VI

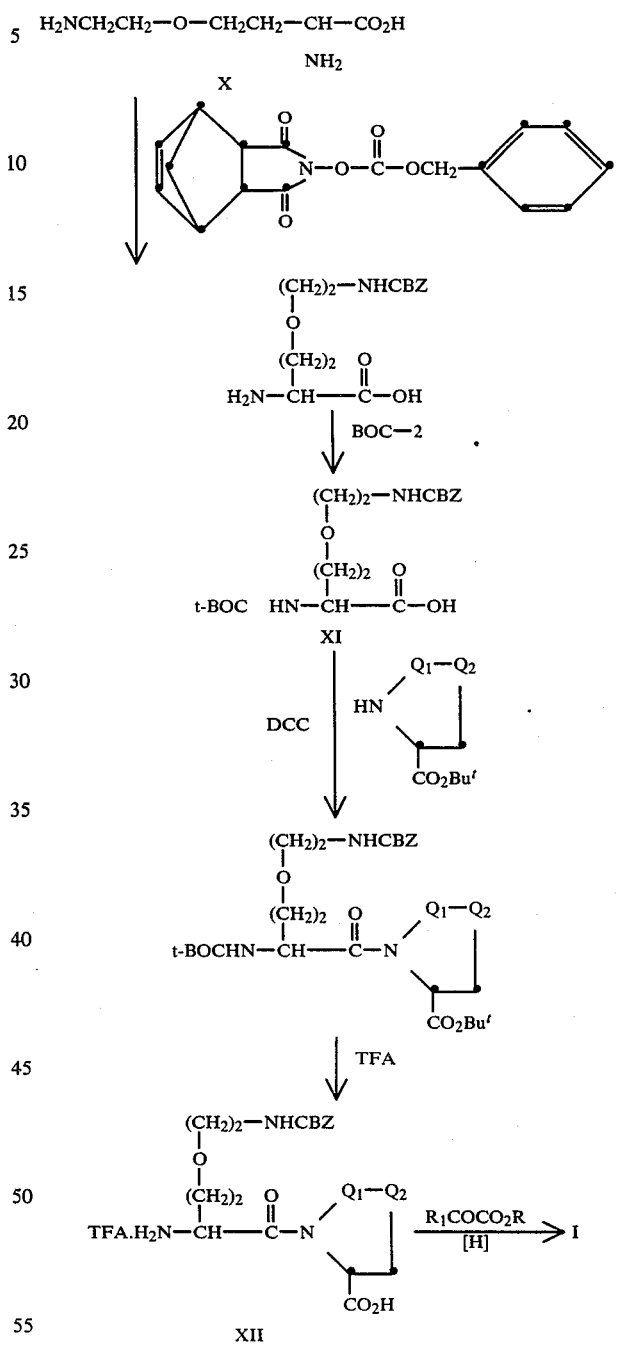

As illustrated in Reaction Scheme I, the synthesis of compounds of Formula I involves the reductive condensation of keto acids or keto esters II with protected dipeptide derivatives III followed by the removal of protecting groups under standard conditions. Typically, this reductive alkylation is conducted using sodium cyanoborohydride under essentially neutral conditions in an aqueous solvent. When X is O, this reductive alkylation can also be conducted using hydrogen in the presence of catalysts such as, for example, palladium on carbon or Raney nickel.

As shown in Reaction Scheme II, it is also possible to conduct this reductive alkylation of II with with amino acids IV (R≠H). Final coupling of intermediate V with amino acids VI is made using reagents standard in peptide chemistry such as, for example, dicyclohexylcarbodiimide, diphenylphosphoryl azide, and the like. Y in the compounds of Reaction Scheme II is a protecting group such as tert-butoxycarbonyl (t-BOC) which can be subsequently removed such as, for example, by treatment with trifluoroacetic acid to yield compounds of Formula I.

Reaction Schemes III, IV and V illustrate syntheses of protected amino acids VII and dipeptide intermediates VIII which involve alkylation and, in the latter case, peptide coupling techniques. In these Reaction Schemes (III, IV and V), CBZ-Cl is carbobenzyloxy chloride, TOS-Cl is tosyl chloride, BOC-2 is di-tert-butyl dicarbonate, DCC is dicyclohexyl carbodiimide, Z is carbobenzyloxy, and TOS is the p-toluene sulfonyl group. In addition, when $Q_1$ and $Q_2$, taken together are $COCH_2$, an acid chloride procedure is used in the amide bond forming step.

As shown in Reaction Scheme III, thialysine and homothialysine (m=3), appropriately protected, are prepared by alkylation of L-cysteine with an acylaminohaloalkane, here illustrated using an N-carbobenzyloxy blocking group on the amino function. The resultant product is further protected on the α-amino group using BOC-2. Coupling of these protected thialysines or homothialysines to a proline ester or analog thereof can be achieved by a variety of reagents such as, for example, dicyclohexyl carbodiimide, diphenylphosphoryl azide, etc., as is well-known to those skilled in the art.

Isomeric homothialysine and bis-homothialysine containing dipeptides are synthesized as shown in Reaction Scheme IV. The methods employed are analogous to those described for Reaction Scheme III except that L-cysteine is replaced by its homolog available as L-homocysteine thiolactone [H. Lindley, *Aust. of Chem.* 12, 296 (1959)]. Shown also is a use of the N-tosyl protecting group.

Reaction Scheme V shows that sulfoxide compounds of Formula I (X=S→O) can be conveniently prepared by treating fully protected compounds IX with m-chloroperbenzoic acid (MCPBA), hydrolysis of the product with suitable acids such as, for example, trifluoroacetic acid (TFA) at room temperature, reductive alkylation and, finally deblocking the desired product with 30% HBr/HOAc.

As illustrated in Reaction Scheme VI, homooxalysine derivatives XI and XII are prepared from the synthesis of 2-amino-4-(2-aminoethoxy)butanoic acid X (J. P. Scannell, et al., *J. Antibiotics,* 29, 38 (1976)). The aminoethoxy group is protected with a benzyloxycarbonyl using N-benzyloxycarbonyloxy-5-norborene-2,3-dicarboximide by the modified method of A. Paquet (*Can. J. Chem.,* 54, 733 (1976)). The $N^2$-amino group is then blocked with tert-butoxycarbonyl using di-tert-butyl dicarbonate in the usual manner. The resulting N-protected homooxalysine XI can be coupled with L-proline-tert-butyl ester in the presence of DCC. Following removal of the tert-butoxycarbonyl and tert-butyl ester groups with TFA, the intermediate XII and $R_1COCO_2R$ are condensed in the presence of sodium cyanoborohydride followed by removal of the benzyloxycarbonyl group in the same manner as described above.

The products of Formula I contain asymmetric carbon atoms and, therefore, can exist as diastereomers or mixtures thereof. Preferred are those products of Formula I in which the amino acid part-structures are in the L-amino acid configuration. In most instances, these configurations can also be designated as having the (S)-absolute configuration. Diastereomeric mixtures are also biologically active and are within the scope of this invention.

The compounds of this invention form salts with various inorganic and organic acids and bases which salts also comprise part of this invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluensulfonic, maleic, fumaric, camphorsulfonic. The non-toxic physiologically acceptable salts are preferred, although other salts are also useful; e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta,* 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.,* 104, 646 (1960) or in a high renin rat model such as that of S. Koletsky et al., *Proc. Soc. Exp. Biol. Med.* 125, 96 (1967).

Thus, the compounds of this invention are useful as antihypertensives in treating hypertensive mammals, including humans, and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage range of 0.5 to 100 mg per patient generally given several times, thus giving a total daily dose of from 0.5 to 400 mg per day. The dose will vary depending on severity of disease, weight of patient and other factors which a person skilled in the art will recognize.

It is often advantageous to administer compounds of this invention in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, ethacrynic acid, furosemide, guanethidene sulfate, hydralazine hydrochloride, hydrochlorothiazide, hydroflumethiazide, metolazone, metroprololtartate, methylclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivalogloxyethyl ester of methyldopa, indacrinone and variable ratios of its enantiomers, nifedipine, verapamil, diltiazem, flumethiazide, bendroflumethiazide, atenolol, (+)-4-{3-{-[2-(1-hydroxycyclohexyl)ethyl]-4-oxo-2-thiazolidinyl}propyl}benzoic acid, bumetanide, prazosin, propanolol, *rauwolfia serpentina,* rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 2.5–100 milligrams per day range can be effectively combined at levels at the 0.5–100 milligrams per day range with the following antihypertensive and diuretic compounds at the indicated per day dose range: hydrochlorothiazide (10–100 mg), timolol (5–60 mg), methyl dopa (65–2000 mg), the pivaloyloxyethyl ester of methyl dopa (30–1000 mg), indacrinone and variable ratios of its enantiomers (25–150 mg) and (+)-4-{3-{[2-1-hydroxycyclohexyl)ethyl]-4-oxo-2-thiazolidinyl}propyl}-benzoic acid (10–100 mg).

In addition, the triple drug combinations of hydrochlorothiazide (10–100 mg) plus amiloride (5–20 mg) plus converting enzyme inhibitor of this invention (0.5–100 mg) or hydrochlorothiazide (10–100 mg) plus timolol (5–60 mg) plus the converting enzyme inhibitor of this invention (0.5–100 mg) are effective combinations to control blood pressure in hypertensive patients.

The above dose ranges will be adjusted on a unit basis as necessary to permit divided daily dosage. Also, the dose will vary depending on the severity of the disease, weight of patient and other factors which a person skilled in the art will recognize.

Typically the combinations shown above are formulated into pharmaceutical compositions as discussed below.

About 0.5 to 100 mg of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by column chromatography or fractional crystallization. Unless otherwise indicated, all temperatures are in degrees Celsius.

EXAMPLE 1

N-[S-(2-Aminoethyl)-N-(1-carboxy-3-phenylpropyl)-L-cysteinyl]-L-proline

S-Benzyloxycarbonylaminoethyl-L-cysteine is prepared from benzyloxycarbonyl-2-iodoethylamine and L-cysteine by the method of H. Lindley (*Austral. J. Chem.,* 12, 296,1959). The α-amino group is protected with tert-butoxycarbonyl using di-tert-butyl dicarbonate. The resulting fully protected S-2-aminoethyl-L-cysteine is condensed with L-proline-tert-butyl ester in the presence of N,N'-dicyclohexylcarbodiimide. This intermediate is readily purified by medium pressure liquid chromatography on silica in ethyl acetate/hexane (1:1).

Treatment of N-tert-butoxycarbonyl-S-benzyloxycarbonyl-aminoethyl-L-cysteinyl-L-proline-tert-butyl ester with trifluoroacetic acid for one hour at room temperature removes the tert-butoxy carbonyl and tert-butyl ester protecting groups. The resulting trifluoroacetate salt (1.44 g., 2.31 mmol) and 2-oxo-4-phenylbutyric acid (2.01 g., 11.3 mmol) are dissolved in ethanol/water (1:1) and adjusted to pH 7 with sodium hydroxide. A solution of sodium cyanoborohydride (426 mg., 6.78 mmol, in 7 ml of water) is added at the rate of 1 ml/hr. by syringe pump. If the presence of unreacted dipeptide is detected after overnight stirring, five more equivalents of the keto acid are added in a minimum of water as the sodium salt. When the reaction is completed, the product is absorbed on Dowex 50

(H+), (50-100 mesh). The ion exchange column is rinsed to neutrality with water, then eluted with 2% pyridine in water. Product-rich fractions are evaporated to dryness then freeze-dried to a white powdery solid.

Removal of the carbobenzoxy group is accomplished by treatment with 30-32% HBr in glacial acetic acid for 15 minutes at room temperature. The resulting HBr salt is absorbed on Dowex 50 (H+). The free amine is eluted from the column with 2% pyridine in water. Evaporation, then freeze-drying of product fractions affords N-[S-(2-aminoethyl)-N-(1-carboxy-3-phenylpropyl)-L-cysteinyl]-L-proline as a white fluffy solid. The nmr spectrum is consistent with structure. The mass spectrum gives a molecular ion at 567 m/e for the disilylated species and a base peak at 477 m/e for loss of the

chain.

EXAMPLE 2

N-[S-(3-Aminopropyl)-N-(1-carboxy-3-phenylpropyl)-L-cysteinyl]-L-proline

Prepare benzyloxycarbonyl-3-bromopropylamine as described for preparing benzyloxycarbonyl-2-bromoethyl-amine in the literature (H. Lindley, Austral. J. Chem., 12, 296, 1959). The crude product (5.20 g.) is reacted with L-cysteine (2.21 g) at pH=9-10 for one hour in the presence of 2% sodium iodide (57 mg.). The product precipitates on acidifying to pH=4.0, then filter and dry. Protect the amino group of S-benzyloxycarbonyl-aminopropyl-L-cysteine (2.60 g.) using di-tert-butyl dicarbonate (1.91 g.) in tert-butanol-H2O. To a mixture of N-tert-butoxycarbonyl-S-benzyloxy-carbonylaminopropyl-L-cysteine (2.75 g.) and L-proline-tert-butyl ester (922 mg.) in methylene chloride at 0° C. was added a solution of dicyclohexylcarbodiimide in methylene chloride and the mixture was stored at 0° C. overnight. After standard extraction work up, purify the crude dipeptide by low pressure liquid chromatography on silica gel (LPS-2, 37-53 μm) with ethyl acetate/hexane (1:1) to obtain pure N-tert-butoxycarbonyl-S-benzyloxycarbonylaminopropyl-L-cysteinyl-L-proline-tert-butyl ester (1.91 g). Deprotect the tert-butoxycarbonyl and tert-butyl ester groups using trifluoroacetic acid (10 ml) at room temperature for one hour to obtain the TFA salt of S-benzyloxycarbonylaminopropyl-L-cysteinyl-L-proline (1.86 g). The reductive alkylation of the TFA salt (1.00 g) with 4-phenyl-2-oxo-butyric acid (1.70 g) in the presence of sodium cyanoborohydride (360 mg) at pH=6.8 is carried out in the usual way. After Dowex 50 (H+) workup, the product (226 mg) is treated with 30-32% HBr/HoAc (5 ml) for 30 minutes at room temperature. Strip off HBr/HoAc then dissolve the residue in 20 ml. H2O/MeOH (5:1) and place on Dowex 50 (H+) column (60 ml). Elute with 2% pyridine-H2O (250 ml) to obtain N-[S-(3-aminopropyl)-N-(1-carboxy-3-phenylpropyl)-L-cysteinyl]-L-proline (178 mg). Further purify by LH-20 chromatography to yield pure product (89 mg). The mass spectrum shows an M+ +1=726 m/e (4TMS) with a parent peak at 711 m/e [M+ −15 (CH3)], 608 m/e [M+ −117 (—CO2TMS)], and 511 m/e [M+ −214

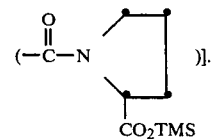

The nmr (D2O) has a spike at 7.2δ (5H, aromatic H), broad multiplets at 4.0-4.35δ (3H, methine H), and multiplets with complex splitting centered about 3.5δ, 3.0δ, 2.8δ and 2.0δ which integrate for 18H.

EXAMPLE 3

N-[S-(2-Aminoethyl)-N-(1-carboxy-3-phenylpropyl)-L-homocysteinyl]-L-proline

S-tosylaminoethyl-L-homocysteine is prepared from N-tosyl-2-iodoethylamine and L-homocysteine (generated in situ by the action of base on L-homocysteine thiolactone.HCl) by the method of H. Lindley (Austral. J. Chem. 12, 296, 1959). The α-amino group is protected with tert-butoxycarbonyl using di-tert-butyl dicarbonate. The tosyl group is removed (with Na/NH3 liq.) and is replaced by CBZ (using CBZ-Cl). The resulting compound, N-tert-butoxycarbonyl-S-benzyloxycarbonyl-aminoethyl-L-homocysteine, is condensed with L-proline-tert-butyl ester in the presence of N,N'-dicyclohexylcarbodiimide. This fully protected intermediate is readily purified by medium pressure liquid chromatography on silica in ethyl acetate/hexane (1:1). Following the removal of the tertbutoxycarbonyl and tert-butyl ester groups with trifluoroacetic acid, the dipeptide and 2-oxo-4-phenylbutyric acid are condensed in the presence of sodium cyanoborohydride in the manner described in Example 1. This reaction is followed by the removal of the carbobenzoxy group with 30-32% HBr in glacial acetic acid to afford N-[S-(2-aminoethyl)-N-(1-carboxy-3-phenylpropyl)-L-homocysteinyl]-L-proline. The nmr spectrum is consistent with structure. The mass spectrum gives a molecular ion at 653 m/e for the trisilylated species and a base peak at 290 m/e for the following fragment plus 1H:

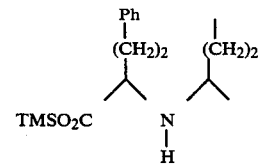

EXAMPLE 4

N-[S-(3-aminopropyl)-N-(1-carboxy-3-phenylpropyl)-L-homocysteinyl]-L-proline

Prepare benzyloxycarbonyl-3-bromopropylamine as described in Example 2. Convert the crude product (4.80 g) to the iodo analog by refluxing an acetone solution (75 ml) containing sodium iodide (2.65 g). React benzyloxycarbonyl-3-iodopropylamine (2.57 g) with L-homocysteine thiolactone.HCl (1.00 g) which was initially dissolved in 1N sodium hydroxide (13.0 ml)/25 ml. ethanol. Acidify to pH=4.0 with 6N HCl. After 1 hour, extract with methylene chloride and strip off organics to give the crude product. Isolation of pure S-benzyloxycarbonylaminopropyl-L-homocysteine (700 mg) is carried out on Dowex 50A (H+) using 10%

NH₃-MeOH as solvent. Protect the α-amino group using di-tert-butyl dicarbonate (463 mg) and couple the resulting N-tert-butylcarbonyl S-benzyloxycarbonylaminopropyl-L-homocysteine (735 mg) with L-proline-tert-butyl ester (333 mg) by the standard DCC method. The crude dipeptide is chromatographed on silica gel (LPS-2, 37–53 μm) under low pressure to give pure N-tert-butoxycarbonyl-S-benzyloxycarbonylaminopropyl-L-homosteinyl-L-proline-tert-butyl ester (78 mg). Deprotection, using trifluoroacetic acid, gives the TFA salt of S-benzyloxycarbonylaminopropyl-L-homocysteinyl-L-proline (53 mg). The reductive alkylation of the TFA salt with 4-phenyl-2-oxo-butyric acid (121 mg) and sodium cyanoborohydride (26 mg) is carried out in the usual manner. The workup, including 30–32% HBr/HOAc treatment, is the same as that described in Example 2. Both ms and nmr are consistent with the structure for N-[S-(3-aminopropyl)-N-(1-carboxy-3-phenylpropyl)-L-homocysteinyl]-L-proline (24 mg). The highest mass is 796 m/e, which is loss of methyl (15) from the desired product ion M⁺ (811=MW+5TMS). Also observed was 739 m/e (MW+4TMS) and 679 m/e which corresponds to a loss of 117 (—CO₂TMS) from 796 m/e.

EXAMPLE 5

N-[S-(2-Aminoethyl)-N-(1-Carboxy-3-phenylpropyl)-L-homocysteinyl]-L-proline

A solution of L-homocystine (5.0 g., 0.0186 mole) in 150 ml of liquid ammonia was treated with sodium metal (1.68 g., 0.0730 mole) until a blue color persisted, and a trace of ammonium chloride was added to dispel the blue color. The solution was cooled to −65° C. until it just began to solidify, and the slurry was treated with benzyloxycarbonyl-2-bromoethylamine (10.0 g., 0.0388 mole) over 2 minutes. The resulting pink slurry was allowed to warm to room temperature overnight to evaporate the ammonia. The remaining white solid was dissolved in 100 ml of water which was filtered and neutralized to pH 7 with 6N hydrochloric acid to precipitate S-[2-(benzyloxycarbonylamino)ethyl]-L-homocysteine; a white solid; nmr (10% NaOD in D₂O): δ1.85 (m, 2H, S—CH₂—CH₂—CH), 2.51 (t, 2H, S—$\underline{CH}$₂—CH₂—CH), 2.68 (t, $\overline{2H}$, aminoethyl—S—$\underline{CH}$₂—), 3.33 (t, 2H,—N$\underline{CH}$₂—), 5.12 (S, 2H, benzyl), 7.41 (S, 5H, aromatic); ms(trimethylsilyl): 369 (M-15), 206 (loss of —CH₂CH₂NHCO₂Bz). The α-amino group was then protected with tert-butoxycarbonyl using di-tert-butyl dicarbonate. The resulting fully protected S-(2-aminoethyl)-L-homocysteine was condensed with L-proline tert-butyl ester in the presence of N,N′-dicyclohexylcarbodiimide. This intermediate was readily purified by a 240×2.5 cm LH-20 column with methanol.

Treatment of N-[S-(2-benzyloxycarbonylaminoethyl)-N-tert-butoxycarbonyl-L-homocysteinyl]-L-proline tert-butyl ester with trifluoroacetic acid for 50 minutes at room temperature removed the tert-butoxycarbonyl and tert-butyl ester protecting groups. The resulting trifluoroacetate salt (0.0012 mole) and 2-oxo-4-phenylbutyric acid (2.00 g., 0.0112 mole) was dissolved in 10 ml of ethanol. After diluting with 10 ml. of water, the solution was neutralized to pH 7 with sodium hydroxide. A solution of sodium cyanoborohydride (0.27 g., 0.0043 mole) in 3.5 ml of ethanol was added dropwise over 14 hours. Chromatography on Dowex 50W using 2% pyridine in water gave 0.36 g. (0.52%) of the product, a white solid on freeze drying.

Removal of the benzyloxycarbonyl group was accomplished by treatment (0.36 g., 0.00063 mole) with 30–32% HBr in glacial acetic acid (25 ml) for 1 hour at room temperature. Purification over Dowex 50W gave 0.273 g. (98%) of N-[S-(2-aminoethyl)-N-(1-carboxy-3-phenylpropyl)-L-homocysteinyl]-L-proline as a white solid on freeze drying; nmr (D₂O): δ1.96 (m, 2H, —CHCH₂CH₂), 2.26 (m, 6H, CH₂$\underline{CH}$₂—, proline C-3 and $\overline{C-4}$), 2.7–3.0 (overlapping, 6H, homocysteine —$\underline{CH}$₂S—, aromatic $\underline{CH}$₂CH₂—, —S—$\underline{CH}$₂CH₂NH₂), $\overline{3.23}$ (t, 2H, —$\underline{CH}$₂NH₂), 3.63 (m, 2H, proline C-5), 7.37 (narrow multiplet, 5H, aromatic); ms (trimethylsilyl): 566 (M+2TMS-methyl).

EXAMPLE 6

(A)

N-[S-(2-(Benzyloxycarbonylaminoethyl)-N-{1-ethoxycarbonyl-3-(2-naphthyl)propyl}-L-homocysteinyl]-L-proline N-[S-(2-Benzyloxycarbonylaminoethyl)-L-homocysteinyl]-L-proline (725 mg., 0.00177 mole) and ethyl 4-(2-naphthyl)-2-oxobutyrate (2.50 g., 0.0098 mole) were stirred with 20 ml of water and the mixture was neutralized to pH 7.0 with sodium hydroxide. After concentrating to dryness in vacuo, the residue was dissolved in 20 ml of ethanol and a solution of sodium cyanoborohydride (0.50 g., 0.008 mole) in 3 ml of ethanol was added dropwise over 16 hours at room temperature. Working over a Dowex 50W Column, followed by chromatography on a 240×0.9 cm LH-20 column with methanol, gave 0.30 g. (26%) of the title compound; an oil; nmr was consistent with structure.

(B)

N-[S-(2-Aminoethyl)-N-{1-carboxy-3-(2-naphthyl)propyl}-L-homocysteinyl]-L-proline The above title (A) compound (0.30 g., 0.00046 mole) was dissolved in 5 ml of ethanol, and the solution was treated with 0.92 ml of 1M sodium hydroxide and was stirred at room temperature for 2 hours. The solution was concentrated to dryness and was flushed several times with ethyl acetate.

The residue from the hydrolysis was treated with 30% hydrogen bromide in glacial acetic acid and then concentrated in vacuo. After purification over Dowex 50W, the mixture was chromatographed on a 240×0.9 cm LH-20 column with methanol to give 0.047 g. (22%) of the desired product; a white solid on freeze drying; nmr (CD₃O): δ1.90 (m, 2H, —SCH₂$\underline{CH}$₂—CH<), 2.2 (m, 6H, Ar—CH₂e,uns/CH/ ₂-proline C-3, C-4), 2.78 (t, 2H, Aromatic-$\underline{CH}$₂CH₂—) 2.95 (2t, 4H, —$\underline{CH}$₂S$\underline{CH}$₂CH₂N$\overline{<}$), 3.16 (m, 2H, 22 N—$\underline{CH}$₂—CH₂—S—), 3.5 (b.m. 2H, proline C-5), 4.1–4.6 (m, 3H,

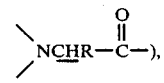

7.44 (m, 3H, β-naphthyl), 7.79 (m, 4H, α-naphthyl), ms (trimethylsilyl): 586 (M+144-CH₃CH₂NH₂), 514 (M+72-CO₂H), 340

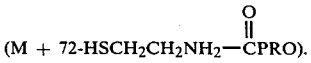

EXAMPLE 7

N-[S-(2-Aminoethyl)-N-{1-carboxy-3-(4-chlorophenyl)propyl}-L-homocysteinyl]-L-proline In the manner described in Examples 3, 5 and 6, 2-oxo-4-(4-chlorophenyl)butyric acid and N-[S-(2-benzyloxycarbonylaminoethyl)-L-homocysteinyl]-L-proline were condensed to afford N-[S-(2-benzyloxycarbonylaminoethyl)-N-{1-carboxy-3-(4-chlorophenyl)-propyl}-L-homocysteinyl]-L-proline. This reaction was followed by the removal of the carbobenzoxy group with 30–32% HBr in glacial acetic acid to give N-[S-(2-aminoethyl)-N-{1-carboxy-3-(4-chlorophenyl)propyl}-L-homocysteinyl]-L-proline in 67% yield; a white solid on freeze drying; ms (trimethylsilyl): 672 (M+3TMS-15), 600 (M+2TMS-15), 570 (M+2TMS-$CO_2H$), 498 (M+1TMS-$CO_2H$).

EXAMPLE 8

N-[S-(2-Aminoethyl)-N-(1-carboxy-3-phenylpropyl)-L-homocysteinyl]-L-proline, S-oxide A stirred solution of N-[S-(2-benzyloxycarbonylaminoethyl)-N-tert-butoxycarbonyl-L-homocysteinyl]-L-proline tert-butyl ester (0.71 g., 0.0013 mole) in 4 ml of methylene chloride at 0° C. was treated dropwise over 45 minutes with a solution of m-chloroperbenzoic acid (0.26 g of 85%, 0.0013 mole) in 8 ml of methylene chloride. An aqueous workup gave 0.78 g (100%) of S-oxide as an oil. A solution of the above S-oxide (0.78 g., 0.0013 mole) in 20 ml of trifluoroacetic acid was stirred at room temperature for 2 hours. A workup, as described in Example 1, gave 0.55 g (100%) of N-[S-(2-benzyloxycarbonylaminoethyl)-L-homocysteinyl]-L-proline; an oily solid. The benzyloxycarbonyl compound (0.55 g., 0.0013 mole) was then reductively alkylated with 2-oxo-4-phenylbutyric acid as described in the above examples. Normal workup, followed by chromatography on LH-20 with methanol gave 0.21 g. (28%) of N-[S-(2-benzyloxycarbonylaminoethyl)-N-(1-carboxy-3-phenylpropyl)-L-homocysteinyl]-L-proline, S-oxide; a white solid after freeze drying. Subsequent removal of benzyloxycarbonyl group with 30–32% HBr/HOAc gave the desired product as a salt which was liberated on Dowex 50 (H$^+$) and further purified on an LH-20 column to give 0.15 g. (100%) of N-[S-(2-aminoethyl)-N-(1-carboxy-3-phenylpropyl)-L-homocysteinyl]-L-proline, S-oxide; ms (trimethylsilyl): 582 (M+2TMS-15); nmr (CD$_3$OD): was consistent with structure.

EXAMPLE 9

N-[S-(2-Aminoethyl)-N-(1-carboxy-3-phenylpropyl)-L-homocysteinyl]-1,2,3,4-tetrahydroisoquinoline-3-(S)-carboxylic acid S-(2-Benzyloxycarbonylaminoethyl)-N-tert-butoxycarbonyl-L-homocysteine (2.14 g., 0.00518 mole) and ethyl 1,2,3,4-tetrahydroisoquinoline-3-(S)-carboxylate (1.12 g., 0.00545 mole) were coupled via the procedure described in Example 5 to give 2.24 g. (72%) of ethyl N-[S-(2-benzyloxycarbonylaminoethyl)-N-tert-butoxycarbonyl-L-homocysteinyl]-1,2,3,4-tetrahydroisoquinoline-3-(S)-carboxylate (1); an oil. Compound 1 (1.10 g., 0.00183 mole) was stirred for 50 minutes at room temperature with 25 ml of trifluoroacetate acid. Concentration in vacuo gave ethyl N-[S-(2-benzyloxycarbonylaminoethyl)-L-homocysteinyl]1,2,3,4-tetrahydroisoquinoline-3-(S)-carboxylate (2) as a crude orange oil. This intermediate (2) was reductively alkylated with 2-oxo-4-phenylbutyric acid (3.00 g., 0.0068 mole) according to the procedure described in Example 5. After chromatography on an LH-20 column with methanol, 0.30 g. (25%) of ethyl N-[S-(2-benzyloxycarbonylaminoethyl)-N-(1-carboxy-3-phenylpropyl)-L-homocysteinyl]-1,2,3,4-tetrahydroisoquinoline-3-(S)-carboxylate (3) was obtained; a colorless oil.

Compound 3 was then hydrolyzed with 30% hydrogen bromide in glacial acetic acid. After purification over LH-20 with methanol, 0.054 g. (25%) of N-[S-(2-aminoethyl)-N-(1-carboxy-3-phenylpropyl)-L-homocysteinyl]-1,2,3,4-tetrahydroisoquinoline-3-(S)-carboxylic acid was obtained; a white solid after freeze drying; nmr (CO$_3$OD): δ2.1–2.25 (m, 4H, aromatic $CH_2CH_2$—, —$SCH_2CH_2CH$<), 2.7–2.9 (m, 8H, aromatic $CH_2CH_2$—, aromatic $CH_2CH$<—CH$_2$S—$\overline{CH_2}$—), 3.0–3.25 (m, 2H, —$SCH_2\overline{CH_2}NH_2$), $\overline{3.32}$ (S, $\overline{2H}$, aromatic $CH_2N$<), 3.5–$\overline{3.8}$ (m, 1H, $\overline{NCHR}CO_2$—), 7.2.–7.3 $\overline{(m}$, 4H, aromatic), ms: M$^+$463.

EXAMPLE 10

N-[S-(2-Aminoethyl)-N-(1-carboxy-3-phenylpropyl)-L-homocysteinyl]-1,2,3,4-tetrahydroisoquinoline-3-(S)-carboxylic acid, S-oxide In the manner described in Example 8, ethyl N-[S-(2-benzyloxycarbonylaminoethyl)-N-tert-butoxycarbonyl-L-homocysteinyl]-1,2,3,4-tetrahydroisoquinoline-3-(S)-carboxylate was oxidized in the presence of m-chloroperbenzoic acid to give S-oxide. Hydrolysis of the product with trifluoroacetic acid at room temperature, reductive alkylation, and finally deblocking with 30% HBr/HOAc as described in Example 9, afforded N-[S-(2-aminoethyl)-N-(1-carboxy-3-phenylpropyl)-L-homocysteinyl]-1,2,3,4-tetrahydroisoquinoline-3-(S)-carboxylic acid, S-oxide. Both mass spectra and nmr were consistent with the desired structure.

EXAMPLE 11

N-[2-{N-(1-Carboxy-3-phenylpropyl)}-4-(2-aminoethoxy)-n-butyryl]-L-proline

2-Amino-4-(2-aminoethoxy)-butanoic acid (4) was synthesized by literature methods (J. P. Scannell, et al., J. Antibiotics 29, 38, 1976).

Crude I (5.67 g., 35.0 mmol) was dissolved in 50 ml of water, treated with 70 ml of 0.5N methanolic potassium hydroxide, and stirred for 1 hour at room temperature with N-benzyloxycarbonyloxy-5-norborene-2,3-dicarboximide (10.95 g., 35.0 mmol). The solution was concentrated in vacuo to remove most of the methanol, diluted with 50 ml of water and neutralized to pH 6.2 with 1N hydrochloric acid. After extracting twice with 10 ml portions of ethyl acetate, the pH was reduced to 1 and extracted twice with 100 ml portions of ethyl acetate. The aqueous solution was passed through a 100 cc column of Dowex 50W which was washed with water and eluted from portions of 2% pyridine/water (100 ml portions). Concentration in vacuo followed by crystallization from 30 ml of methanol gave 0.95 g. of 2-amino-4-(2-benzyloxycarbonylaminoethoxy)-butanoic acid (5). LH-20 chromatography yielded an additional 0.23 g. of 5 for a total of 1.18 g. (11%) of 5; a white solid; nmr (TFA): δ2.1–2.6 (br.m., 2H, O$CH_2CH_2CH$<), 3.5–4.1 (m, 6H, —$CH_2OCH_2CH_2NH$—), 4.1–4.9 (m, 1H, $H_2NCHRCO_2$—), 5.27 (S, 2H, —$CH_2\phi$), 7.4 (s, 5H, aromatic).

Compound 5 (1.18 g., 4.0 mmol) was dissolved in a mixture of 4.0 ml of 1M sodium hydroxide, 15 ml of tert-butyl alcohol, and 10 ml of water. After cooling to 15° C., di-tert-butyl dicarbonate (0.93 g., 4.25 mmol) was added and the mixture was allowed to warm to temperature over 1.5 hours. The clear solution was filtered and the pH was reduced to 2.0 with concentrated hydrochloric acid. The gum which formed was extracted with 2×100 ml of ethyl aetate. Concentration in vacuo gave 1.58 g. (100%) of 2-tert-butoxycarbonylamino-4-(2-benzyloxycarbonylaminoethoxy)-butanoic acid (6); a colorless oil; nmr (CCl4): δ1.41 (S, 9H, t-butyl), 1.8–22 (m, 2H, —OCH2C$\underline{H_2}$CH<), 3.1–3.7 (m, 6H, —C$\underline{H_2}$OC$\underline{H_2}$CH2N<), 4.0–4.6 (m, 1H, —NHC$\underline{H}$RCO2—), 5.03 (s, 2H, —C$\underline{H_2}$Ø), 7.22 (s, 5H, aromatic).

Compound 6 (1.58 g., 4.0 mmol) and L-proline tert-butyl ester (0.75 g., 4.39 mmol) were dissolved in 25 ml of dichloromethane. The solution was cooled to 0° C. and N,N'-dicyclohexylcarbodiimide (0.90 g., 4.39 mmol) was added in one portion. The mixture was stirred at 0° C. for 1 hour and was allowed to warm to room temperature overnight. Work up in the usual way, gave N-[2-tert-butoxycarbonylamino-4-(2-benzyloxycarbonylaminoethoxy)-n-butyryl]-L-proline tert-butyl ester. Following the removal of the tert-butoxycarbonyl and tert-butyl ester groups with trifluoroacetic acid, the intermediate and 2-oxo-4-phenylbutyric acid were condensed in the presence of sodium cyanoborohydride followed by benzyloxycarbonyl group removal in the manner described in the above examples to afford N-[2-{N-(1-carboxy-3-phenylpropyl)}-4-(2-aminoethoxy)-n-butyryl]-L-proline. The mass spectrum showed a molecular ion at 709 m/e for the tetrasilylated species.

EXAMPLE 12

Additional Products of Formula I

Using methods illustrated in the foregoing Examples, it is possible to prepare dipeptide intermediates of Formula III as listed in Table I below. In these syntheses suitably protected known amino acids are coupled to protected, heteroatom substituted diamino acids of Formula IV as described in these Examples. Peptides containing pyroglutamic acid are preferably synthesized by an acid chloride procedure.

Known keto acids or esters listed in Table II are reductively condensed with protected dipeptides of Formula III using sodium cyanoborohydride to yield products of Formula I as illustrated in Examples 1–11 above. The removal of protecting groups can be achieved under standard conditions as is also described in these examples.

TABLE I

Dipeptide Intermediates of Formula III:

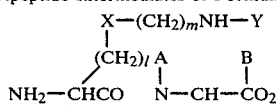

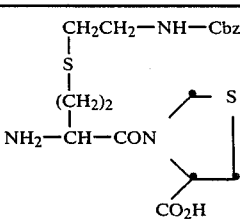
(a)

TABLE I-continued

Dipeptide Intermediates of Formula III:

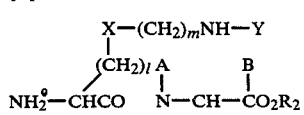

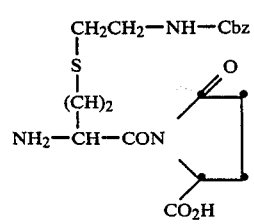
(b)

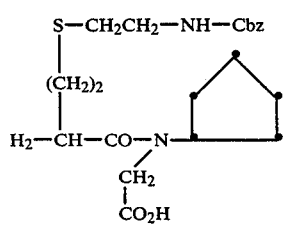
(c)

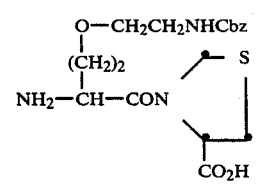
(d)

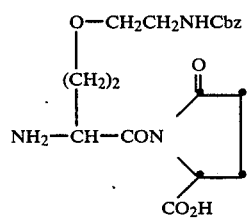
(e)

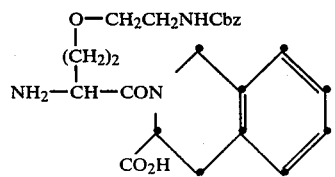
(f)

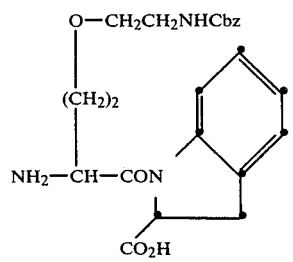
(g)

TABLE I-continued
Dipeptide Intermediates of Formula III:
$$\begin{array}{c} X-(CH_2)_m NH-Y \\ | \\ (CH_2)_l \; A \quad\quad B \\ | \quad\quad | \quad | \\ NH_2-CHCO \quad N-CH-CO_2R_2 \end{array}$$
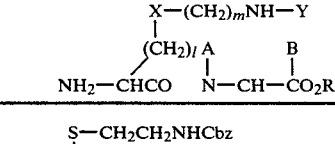 (h)
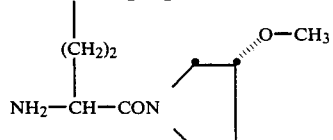 (i)
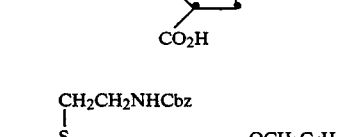 (j)
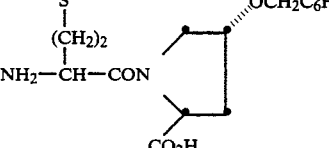 (k)
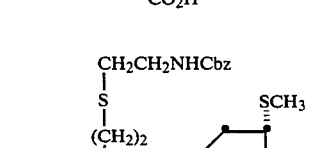 (l)
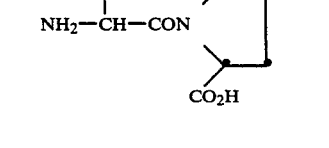 (m)
TABLE II
Keto Acids and Esters of Formula II:
$R_1CO-CO_2R$
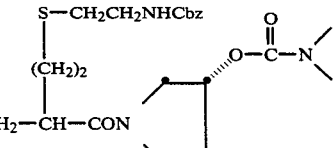 (n)
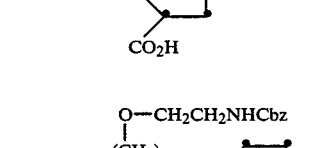 (o)
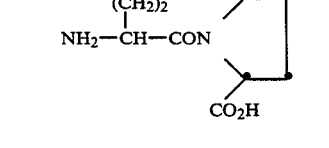 (p)
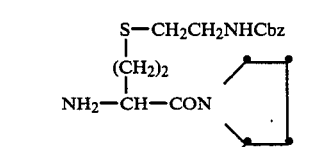 (q)
$CH_3-SCH_2CH_2COCO_2H$ (r)
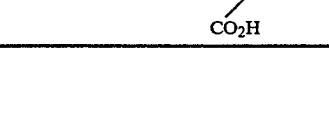 (s)
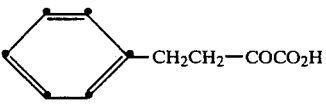 (t)
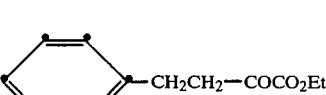 (u)
 (v)
$\begin{array}{c} CH_3 \\ \phantom{C}\diagdown \\ CH-CH_2CH_2-CO-CO_2CH_3 \\ \phantom{C}\diagup \\ CH_3 \end{array}$ (w)
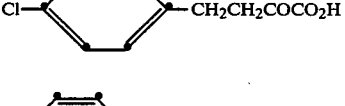 (x)
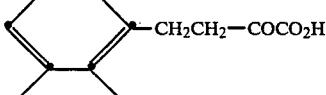 (y)

TABLE III
Products of Formula I:
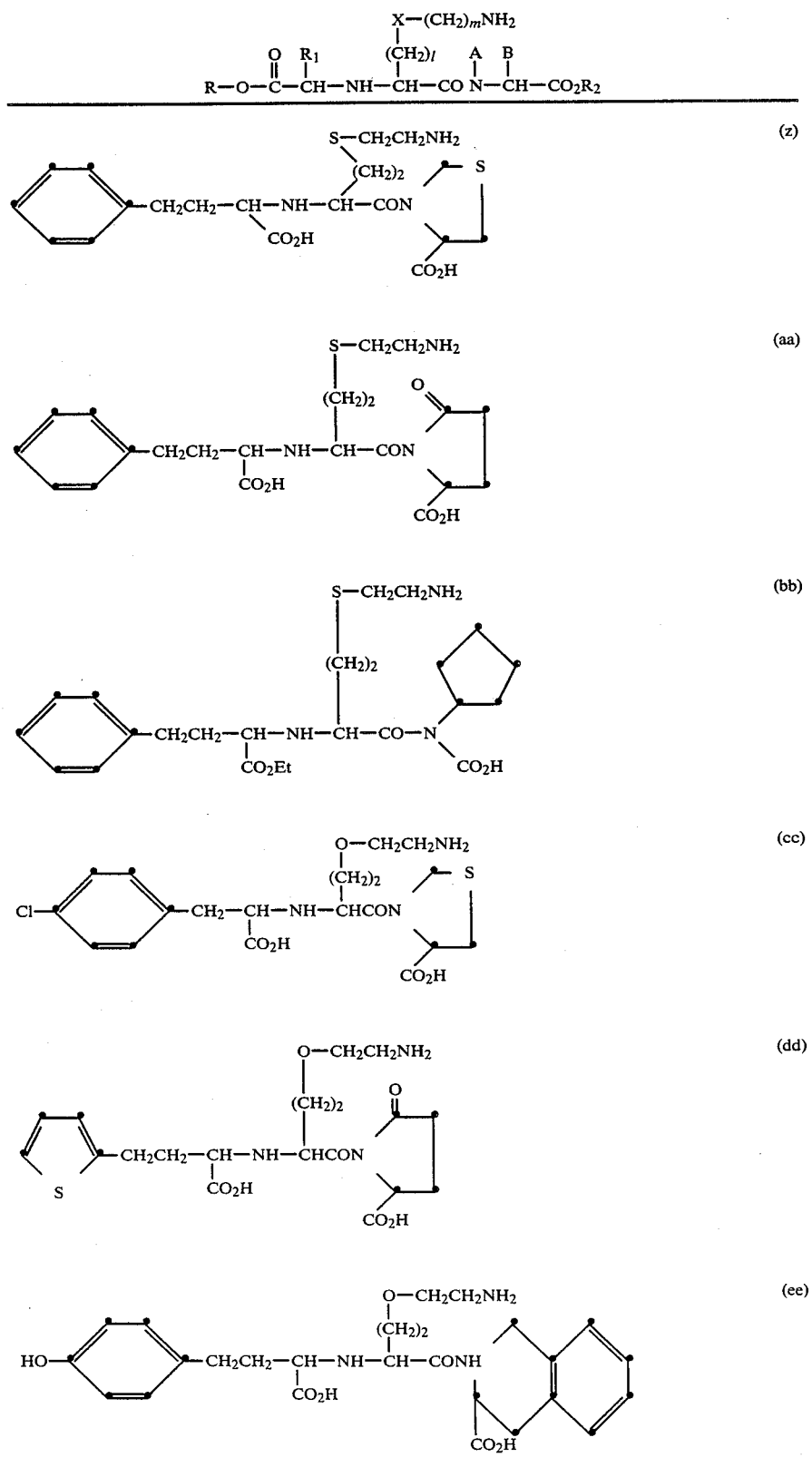

TABLE III-continued
Products of Formula I:
$$R-O-\overset{O}{\underset{\|}{C}}-\overset{R_1}{\underset{|}{CH}}-NH-\overset{(CH_2)_l}{\underset{|}{CH}}-CO\overset{X-(CH_2)_mNH_2}{\underset{B}{\overset{A}{N}-\underset{|}{CH}-CO_2R_2}}$$
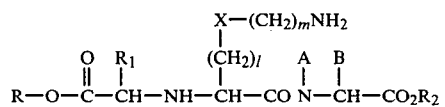
(ff)
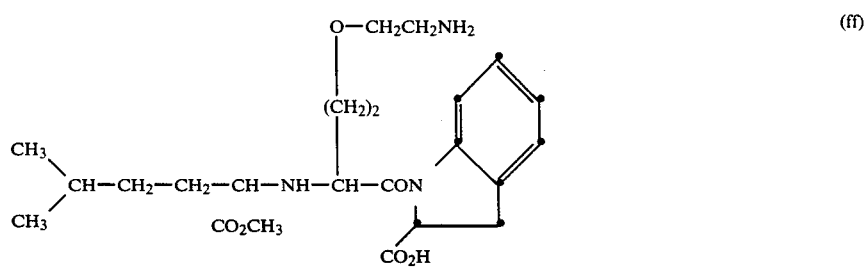
(gg)
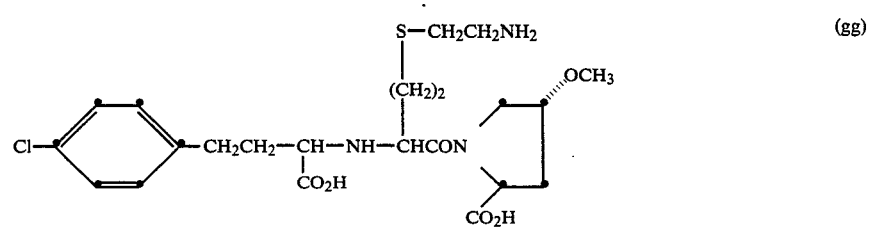
(hh)
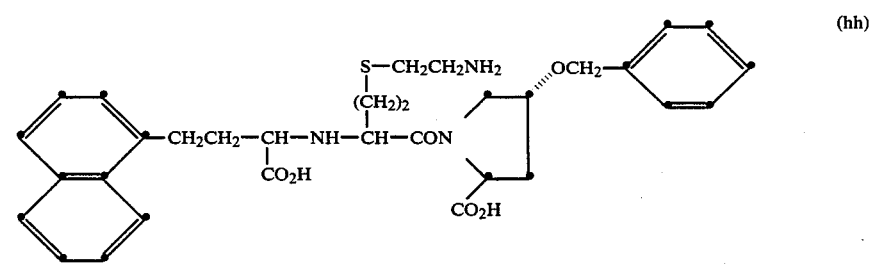
(ii)
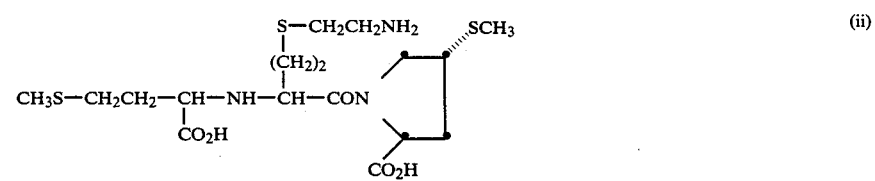
(jj)
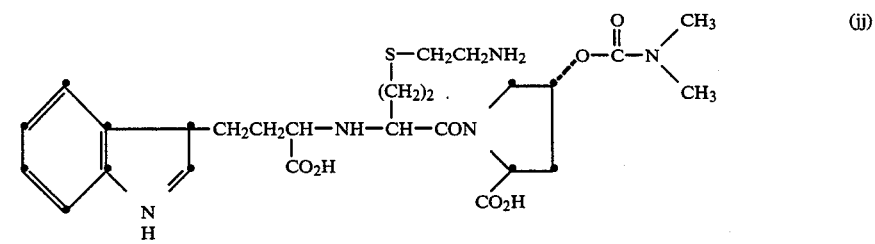
(kk)
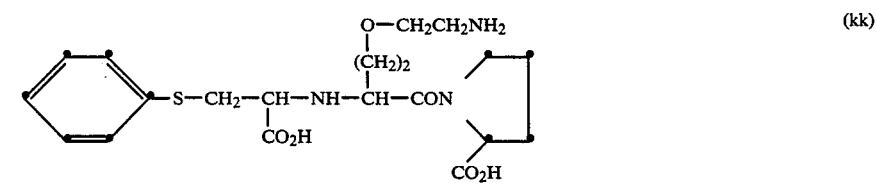

TABLE III-continued

Products of Formula I:

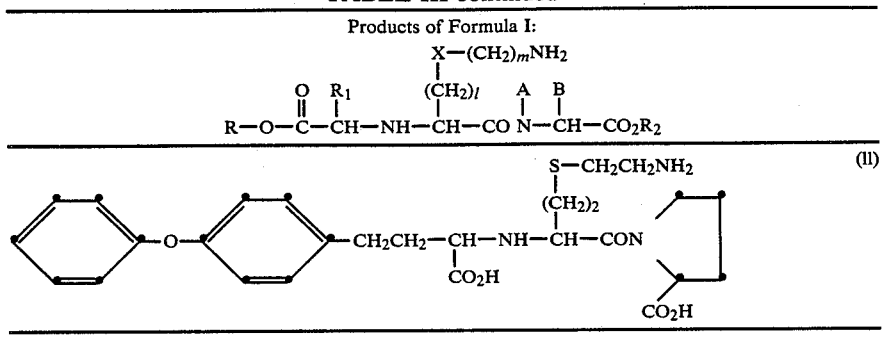

What is claimed is:
1. A compound of the formula:

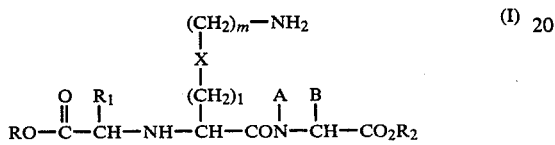

wherein:
R and $R_2$ are independently hydrogen, loweralkyl, aralkyl;
$R_1$ is alkyl containing one to ten carbon atoms which include straight chain, branched, unsaturated and cyclic alkyl groups; substituted lower alkyl wherein the alkyl group has 1-6 carbon atoms and the substituent is amino, acylamino, loweralkylthio, arylthio, aryloxy, arylamino, or hydroxy; aralkyl, aralkenyl, heteroaralkyl or heteroaralkenyl wherein the alkyl portion has 1 to 5 carbon atoms such as, for example, phenethyl, cinnamyl, or indolylethyl; substituted aralkyl, aralkenyl, heteroaralkyl, or heteroaralkenyl wherein the alkyl or alkenyl group has 1 to 5 carbons optionally substituted by amino, acylamino or hydroxy and wherein the aryl of heteroaryl groups are optionally substituted by halo, dihalo, amino, aminoalkyl, hydroxy, lower alkoxy, aryloxy or lower alkyl;
X is S,
l is 1-2;
m is 2-3;

is a grouping wherein:
A is cycloalkyl containing 4-8 carbons in the ring, aryl, aralkyl, heteroaryl, or heteroaralkyl;
B is hydrogen or loweralkyl; or
A and B can be joined together to form ring structures, including the part-structure N—CH—$CO_2R_2$, having the formulae:

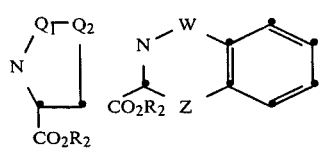

wherein:

$Q_1$ and $Q_2$, taken together, are $CH_2CH_2$, $CH_2CH_2CH_2$, $COCH_2$, $CH_2S$, $CH_2$—CH—$OR_3$, or $CH_2$—CH—$SR_3$ wherein $R_3$ is hydrogen, loweralkyl, aryl, aralkyl, or

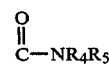

wherein $R_4$ and $R_5$ are independently hydrogen, loweralkyl, or aralkyl;
W is a bond, CO, $CH_2$;
Z is a bond except when W is a bond, CO, $CH_2$, $CH_2CH_2$;
and, the pharmaceutically acceptable salts thereof.
2. A compound of claim 1 wherein:
R and $R_2$ are independently hydrogen, lower alkyl, aralkyl;
$R_1$ is alkyl containing one to eight carbon atoms both straight chain and branched; substituted loweralkyl wherein the alkyl group has 1-3 carbons and the substituent is arylthio, aryloxy; aralkyl, aralkenyl, heteroaralkyl, or heteroaralkenyl wherein the alkyl group has 1 to 5 carbon atoms and the aryl or heteroaryl group can be substituted by halo, dihalo, amino, aminoalkyl, hydroxy, loweralkoxy, aryloxy, or loweralkyl;
X is S;
l is 1 or 2;
m is 2 or 3; and,
A and B are joined together to form ring structures having the formulae:

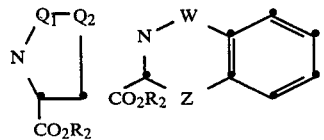

wherein:
$Q_1$ and $Q_2$, taken together, are $CH_2CH_2$, $CH_2S$, $COCH_2$, or $CH_2CHOR_3$ wherein $R_3$ is hydrogen or loweralkyl.
3. A compound of claim 1 wherein:
R and $R_2$ are hydrogen;
$R_1$ is aralkyl and heteroaralkyl wherein the alkyl group has 1 to 3 carbon atoms and the aryl or heteroaryl group can be substituted by halo, dihalo, amino, aminoalkyl, hydroxy, lower alkoxy or lower alkyl;
X is S;
l is 1 or 2;

m is 2 or 3;

A and B are joined together to form ring structures having the formulae:

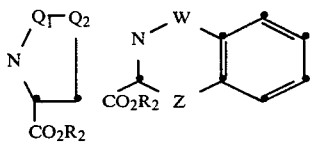

wherein:

$Q_1$ and $Q_2$, taken together, are $CH_2CH_2$, $CH_2S$, $COCH_2$, or $CH_2CHOR_3$ wherein $R_3$ is loweralkyl;

W is $CH_2$; and

Z is $CH_2$.

4. A compound of claim 1 wherein:

R and $R_2$ are hydrogen;

$R_1$ is aralkyl or heteroaralkyl wherein the alkyl group has 1–4 carbon atoms and the aryl or heteroaryl groups can be substituted by halo or hydroxy;

X is S;

l is 2;

m is 2;

A and B are joined together to form ring structures having the formulae:

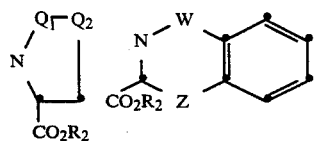

wherein:

$Q_1$ and $Q_2$, taken together, are $CH_2CH_2$ and $CH_2S$;

W is $CH_2$; and,

Z is $CH_2$.

5. A compound of claim 4 which is N-[S-(2-aminoethyl)-N-(1-carboxy-3-phenylpropyl)-L-cysteinyl]-L-proline.

6. A compound of claim 4 which is N-[S-(2-aminoethyl)-N-[1(S)-carboxy-3-phenylpropyl]-L-cysteinyl]-L-proline.

7. A compound of claim 4 which is N-[S-(2-aminoethyl)-N-(1-carboxy-3-phenylpropyl)-L-homocysteinyl]-L-proline.

8. A compound of claim 4 which is N-[S-(2-aminoethyl)-N-(1(S)-carboxy-3-phenylpropyl)-L-homocysteinyl]-L-proline.

9. A pharmaceutical composition useful in the treatment of hypertension which comprises a pharmaceutically acceptable carrier and an antihypertensively effective amount of a compound of the formula:

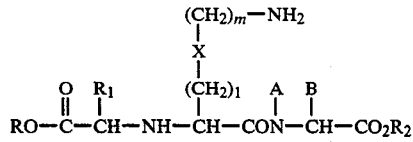 (I)

wherein:

R and $R_2$ are independently hydrogen, loweralkyl, aralkyl;

$R_1$ is alkyl containing one to ten carbon atoms which include straight chain, branched, unsaturated and cyclic alkyl groups; substituted lower alkyl wherein the alkyl group has 1–6 carbon atoms and the substituent is amino, acylamino, loweralkylthio, arylthio, aryloxy, arylamino, or hydroxy; aralkyl, aralkenyl, heteroaralkyl or heteroaralkenyl wherein the alkyl portion has 1 to 5 carbon atoms such as, for example, phenethyl, cinnamyl, or indolylethyl; substituted aralkyl, aralkenyl, heteroaralkyl, or heteroaralkenyl wherein the alkyl or alkenyl group has 1 to 5 carbons optionally substituted by amino, acylamino or hydroxy and wherein the aryl or heteroaryl groups are optionally substituted by halo, dihalo, amino, aminoalkyl, hydroxy, lower alkoxy, aryloxy or lower alkyl;

X is S, l is 1–2;

m is 2–3;

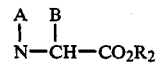

is a grouping wherein:

A is cycloalkyl containing 4–8 carbons in the ring, aryl, aralkyl, heteroaryl, or heteroaralkyl;

B is hydrogen or loweralkyl; or

A and B can be joined together to form ring structures, including the part-structure N—CH—CO$_2$R$_2$, having the formulae:

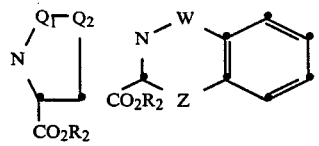

wherein:

$Q_1$ and $Q_2$, taken together, are $CH_2CH_2$, $CH_2CH_2CH_2$, $COCH_2$, $CH_2S$, $CH_2$—CH—OR$_3$, or $CH_2$—CH—SR$_3$ wherein $R_3$ is hydrogen, loweralkyl, aryl, aralkyl, or

wherein $R_4$ and $R_5$ are independently hydrogen, loweralkyl, or aralkyl;

W is a bond, CO, $CH_2$;

Z is a bond except when W is a bond, CO, $CH_2$, $CH_2CH_2$;

and, the pharmaceutically acceptable salts thereof.

10. The composition of claim 9 wherein said compound is a member of the group:

N-S-[(2-aminoethyl)-N-(1-carboxy-3-phenylpropyl)-L-cysteinyl]-L-proline;

N-[S-(2-aminoethyl)-N-[1(S)-carboxy-3-phenylpropyl]-L-cysteinyl]-L-proline;

N-[S-(2-aminoethyl)-N-(1-carboxy-3-phenylpropyl)-L-homocysteinyl]-L-proline; and, N-[S-(2-aminoethyl)-N-(1(S)-carboxy-3-phenylpropyl)-L-homocysteinyl]-L-proline.

11. A pharmaceutical composition useful in the treatment of hypertension which comprises a pharmaceutically acceptable carrier; an antihypertensively effective amount of a compound of the formula:

$$\begin{array}{c} (CH_2)_m-NH_2 \\ | \\ X \\ | \\ \underset{RO-C-CH-NH-CH-CON-CH-CO_2R_2}{\overset{O}{\|}\ \ \ \overset{R_1}{|}\ \ \ \ \ \ \overset{(CH_2)_l}{|}\ \ \overset{A}{|}\ \overset{B}{|}} \end{array} \quad (I)$$

wherein:

R and $R_2$ are independently hydrogen, loweralkyl, aralkyl;

$R_1$ is alkyl containing one to ten carbon atoms which include straight chain, branched, unsaturated and cyclic alkyl groups; substituted lower alkyl wherein the alkyl group has 1–6 carbon atoms and the substituent is amino, acylamino, loweralkylthio, arylthio, aryloxy, arylamino, or hydroxy; aralkyl, aralkenyl, heteroaralkyl or heteroaralkenyl wherein the alkyl portion has 1 to 5 carbon atoms such as, for example, phenethyl, cinnamyl, or indolylethyl; substituted aralkyl, aralkenyl, heteroaralkyl, or heteroaralkenyl wherein the alkyl or alkenyl group has 1 to 5 carbons optionally substituted by amino, acylamino or hydroxy and wherein the aryl or heteroaryl groups are optionally substituted by halo, dihalo, amino, aminoalkyl, hydroxy, lower alkoxy, aryloxy or lower alkyl;

X is S, l is 1–2;

m is 2–3;

$$\begin{array}{c} A\ \ B \\ |\ \ \ | \\ N-CH-CO_2R_2 \end{array}$$

is a grouping wherein:

A is cycloalkyl containing 4–8 carbons in the ring, aryl, aralkyl, heteroaryl, or heteroaralkyl;

B is hydrogen or loweralkyl; or

A and B can be joined together to form ring structures, including the part-structure N—CH—CO$_2$R$_2$, having the formulae:

$$\begin{array}{cc} \underset{CO_2R_2}{\overset{Q_1-Q_2}{\diagup\phantom{xxx}\diagdown}} & \underset{CO_2R_2\ \ Z}{\overset{W}{\diagup\phantom{xx}\diagdown}} \end{array}$$

wherein:

$Q_1$ and $Q_2$, taken together, are $CH_2CH_2$, $CH_2CH_2CH_2$, $COCH_2$, $CH_2S$, $CH_2$—CH—$OR_3$, or $CH_2$—CH—$SR_3$ wherein $R_3$ is hydrogen, loweralkyl, aryl, aralkyl, or $$\begin{array}{c} O \\ \| \\ C-NR_4R_5 \end{array}$$

wherein $R_4$ and $R_5$ are independently hydrogen, loweralkyl, or aralkyl;

W is a bond, CO, $CH_2$;

Z is a bond except when W is a bond, CO, $CH_2$, $CH_2CH_2$;

the pharmaceutically acceptable salts thereof; and, another antihypertensive and/or diuretic compound selected from amiloride, atenolol, bendroflumethiazide, chlorothalidone, chlorothiazide, clonidine, cryptenamine acetae and cryptenamine tannates, deserpidine, diazoxide, ethacrynic acid, furosemide, guanethidene sulfate, hydralazine hydrochloride, hydrochlorothiazide, hydroflumethiazide, metolazone, metroprololtartate, methylclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivalogloxyethyl ester of methyldopa, indacrinone and variable ratios of its enantiomers, nifedipine, verapamil, diltiazam, flumethiazide, bendroflumethiazide, atenolol, (+)-4-{3-{-[2-(1-hydroxycyclohexyl)ethyl]-4-oxo-2-thiazolidinyl}propyl}benzoic acid, bumetanide, prazosin, propranolol, *rauwolfia serpentina*, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

12. The composition of claim 11 wherein said pharmaceutical compound is a member of the group:

N-[S-(2-aminoethyl)-N-(1-carboxy-3-phenylpropyl-L-cysteinyl]-L-proline;

N[-S-(2-aminoethyl)-N-[1(S)-carboxy-3-phenylpropyl]-L-cysteinyl]-L-proline;

N-[S-(2-aminoethyl)-N-(1-carboxy-3-phenylpropyl)-L-homocysteinyl]-L-proline; and, N-[S-(2-aminoethyl)-N-(1(S)-carboxy-3-phenylpropyl)-1-homocysteinyl]-L-proline.

13. A method for treating hypertension which comprises administering to a patient in need of such treatment an antihypertensively effective amount of a compound of the formula:

$$\begin{array}{c} (CH_2)_m-NH_2 \\ | \\ X \\ | \\ \underset{RO-C-CH-NH-CH-CON-CH-CO_2R_2}{\overset{O}{\|}\ \ \ \overset{R_1}{|}\ \ \ \ \ \ \overset{(CH_2)_l}{|}\ \ \overset{A}{|}\ \overset{B}{|}} \end{array} \quad (I)$$

wherein:

R and $R_2$ are independently hydrogen, loweralkyl, aralkyl;

$R_1$ is alkyl containing one to ten carbon atoms which include straight chain, branched, unsaturated and cyclic alkyl groups; substituted lower alkyl wherein the alkyl group has 1–6 carbon atoms and the substituent is amino, acylamino, loweralkylthio, arylthio, aryloxy, arylamino, or hydroxy; aralkyl, aralkenyl, heteroaralkyl or heteroaralkenyl wherein the alkyl portion has 1 to 5 carbon atoms such as, for example, phenethyl, cinnamyl, or indolylethyl; substituted aralkyl, aralkenyl, heteroaralkyl, or heteroaralkenyl wherein the alkyl or alkenyl group has 1 to 5 carbons optionally substituted by amino, acylamino or hydroxy and wherein the aryl or heteroaryl groups are optionally substituted by halo, dihalo, amino, aminoalkyl, hydroxy, lower alkoxy, aryloxy or lower alkyl;

X is S, l is 1–2;

m is 2–3;

$$\begin{array}{c} A\ \ B \\ |\ \ \ | \\ N-CH-CO_2R_2 \end{array}$$

is a grouping wherein:

A is cycloalkyl containing 4–8 carbons in the ring, aryl, aralkyl, heteroaryl, or heteroaralkyl;

B is hydrogen or loweralkyl; or

A and B can be joined together to form ring structures, including the part-structure N—CH—CO$_2$R$_2$, having the formulae:

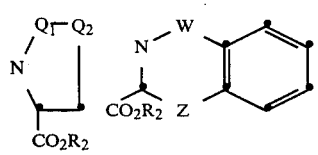

wherein:

Q$_1$ and Q$_2$, taken together, are CH$_2$CH$_2$, CH$_2$CH$_2$CH$_2$, COCH$_2$, CH$_2$S, CH$_2$—CH—OR$_3$, or CH$_2$—CH—SR$_3$ wherein R$_3$ is hydrogen, loweralkyl, aryl, aralkyl, or

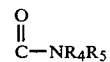

wherein R$_4$ and R$_5$ are independently hydrogen, loweralkyl, or aralkyl;

W is a bond, CO, CH$_2$;

Z is a bond except when W is a bond, CO, CH$_2$, CH$_2$CH$_2$;

and, the pharmaceutically acceptable salts thereof.

14. The method of claim 13 wherein said antihypertensively effective compound is selected from the group:

N-[S-(2-aminoethyl)-N-(1-carboxy-3-phenylpropyl)-L-cysteinyl]-L-proline;

N-[S-(2-aminoethyl)-N-[1(S)-carboxy-3-phenylpropyl]-L-cysteinyl]-L-proline;

N-[S-(2-aminoethyl)-N-(1-carboxy-3-phenylpropyl)-L-homocysteinl]-L-proline; and, N-[S-(2-aminoethyl)-N-(1(S)-carboxy-3phenylpropyl)-L-homocysteinyl]-L-proline.

* * * * *